United States Patent
Silva et al.

(10) Patent No.: US 12,295,784 B2
(45) Date of Patent: May 13, 2025

(54) SYSTEM AND METHOD FOR AUGMENTED REALITY DATA INTERACTION FOR ULTRASOUND IMAGING

(71) Applicant: Washington University, St. Louis, MO (US)

(72) Inventors: Jonathan Silva, St. Louis, MO (US); Christopher Andrews, Chesterfield, MO (US); Jennifer Silva, St. Louis, MO (US); Zahid Iqbal, Kirkwood, MO (US)

(73) Assignee: Washington University, St. Louis, MO (US)

( * ) Notice: Subject to any disclaimer, the term of this patent is extended or adjusted under 35 U.S.C. 154(b) by 215 days.

(21) Appl. No.: 17/799,826

(22) PCT Filed: Apr. 13, 2021

(86) PCT No.: PCT/US2021/027064
§ 371 (c)(1),
(2) Date: Aug. 15, 2022

(87) PCT Pub. No.: WO2021/211570
PCT Pub. Date: Oct. 21, 2021

(65) Prior Publication Data
US 2023/0065505 A1     Mar. 2, 2023

Related U.S. Application Data

(60) Provisional application No. 63/008,997, filed on Apr. 13, 2020.

(51) Int. Cl.
*A61B 8/00*     (2006.01)
*A61B 34/20*    (2016.01)

(52) U.S. Cl.
CPC ............... *A61B 8/42* (2013.01); *A61B 34/20* (2016.02); *A61B 8/4416* (2013.01)

(58) Field of Classification Search
CPC ......... A61B 8/42; A61B 34/20; A61B 8/4416; A61B 90/96; A61B 2017/00207;
(Continued)

(56) References Cited

U.S. PATENT DOCUMENTS 7,835,785 B2 * 11/2010 Scully ................... A61B 5/062
                                                    600/424
9,561,019 B2 *  2/2017 Mihailescu .......... A61B 6/4258
(Continued)

FOREIGN PATENT DOCUMENTS

WO     2019051464 A1     3/2019

OTHER PUBLICATIONS

European Extended Search Report issued in European Application No. 217883913.7 mailed on Jan. 11, 2024, pp. 1-8.
(Continued)

*Primary Examiner* — Sanjay Cattungal
(74) *Attorney, Agent, or Firm* — Armstrong Teasdale LLP

(57) ABSTRACT

A mixed reality (MR) visualization system includes an MR device comprising a holographic display configured to display a holographic image to an operator, a hand-held ultrasound imaging device configured to obtain a real-time ultrasound image of a subject's anatomy, and a computing device communicatively coupled to the MR device and the hand-held ultrasound imaging device. The computing device includes a non-volatile memory and a processor. The computing device is configured to receive the real-time ultrasound image, determine a real-time 3D position and orientation of the hand-held ultrasound imaging device, generate a modified real-time ultrasound image by modifying the real-time ultrasound image to correspond to the real-time 3D
(Continued)

position and orientation of the hand-held ultrasound imaging device, and transmit the modified real-time ultrasound image to the MR device for display as the holographic image positioned at a predetermined location relative to the hand-held ultrasound imaging device.

24 Claims, 8 Drawing Sheets

(58) Field of Classification Search
CPC .. A61B 2017/00216; A61B 2034/2048; A61B 2034/2051; A61B 2034/2055; A61B 2034/2065; A61B 2090/365; A61B 2090/372; A61B 2090/378; A61B 2090/502; A61B 8/4245; A61B 8/469; A61B 90/36; A61B 90/37; A61B 90/50; A61B 2017/00203; G06T 19/00; G06T 2210/41; G06T 19/006; A61M 25/0108; A61M 2025/0166; G16H 30/40; G16H 50/50; G16H 20/40; G16H 40/63
See application file for complete search history.

(56) References Cited

U.S. PATENT DOCUMENTS

| | | | |
|---|---|---|---|
| 9,861,446 B2* | 1/2018 | Lang | A61B 17/1778 |
| 10,258,427 B2 | 4/2019 | Saget et al. | |
| 11,497,436 B1* | 11/2022 | Roh | A61B 5/4509 |
| 2008/0208055 A1* | 8/2008 | Bertram | A61B 34/20 600/443 |
| 2008/0281206 A1* | 11/2008 | Bartlett | A61B 8/56 600/459 |
| 2014/0358002 A1 | 12/2014 | Daoura | |
| 2017/0258526 A1* | 9/2017 | Lang | A61B 17/1775 |
| 2019/0339525 A1 | 11/2019 | Yanof et al. | |

OTHER PUBLICATIONS

PCT International Search Report and Written Opinion for Patent Application PCT/US2021/027064 mailed Jul. 22, 2021; 8 pp.

* cited by examiner

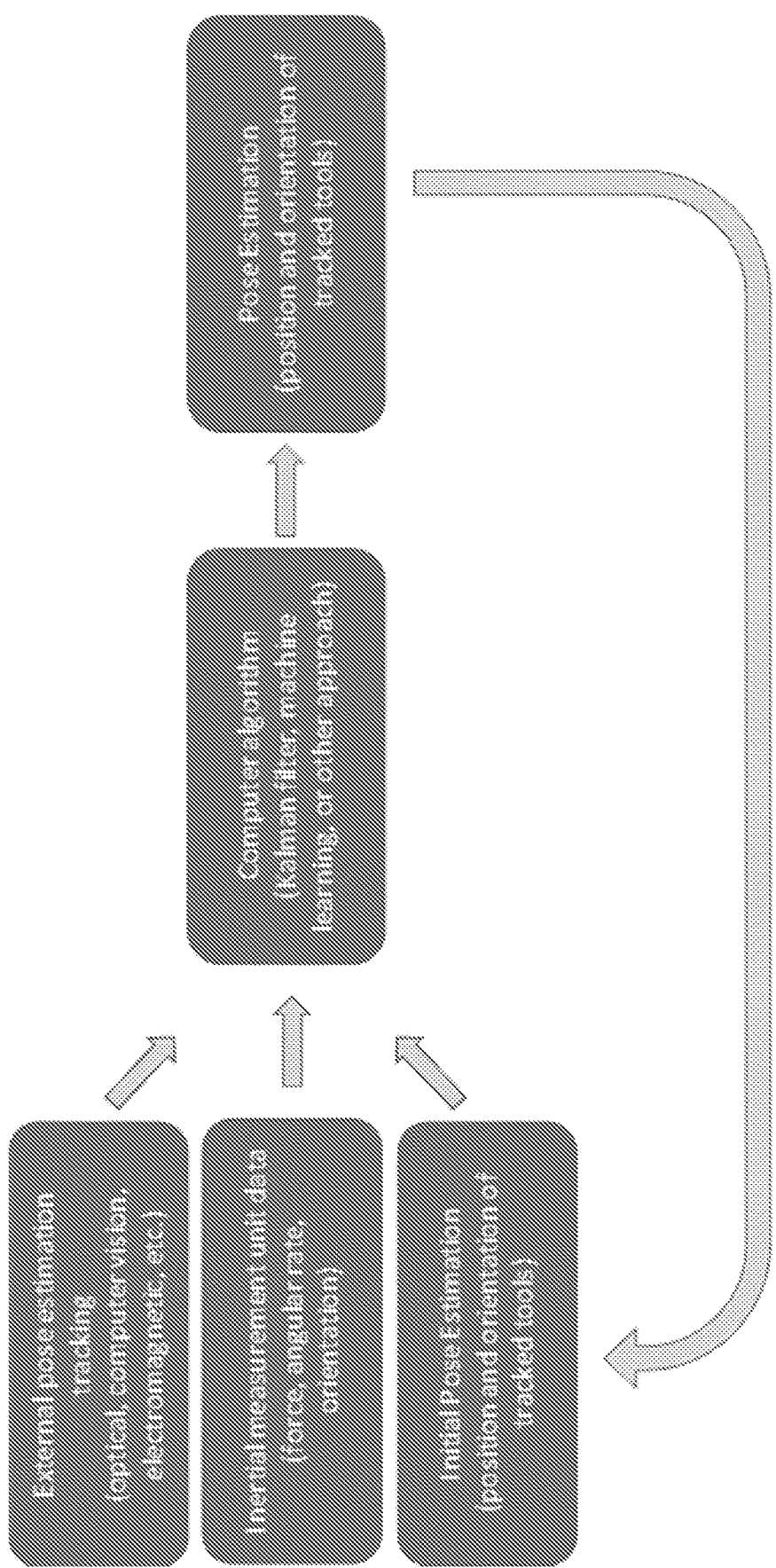

SYSTEM AND METHOD FOR AUGMENTED REALITY DATA INTERACTION FOR ULTRASOUND IMAGING

CROSS-REFERENCE TO RELATED APPLICATION

This application is a U.S. National Phase Patent Application of PCT/US2021/027064 filed Apr. 13, 2021, which claims priority to U.S. Provisional Patent Application No. 63/008,997 filed Apr. 13, 2020, the entire disclosures of both of which are hereby incorporated by reference in their entireties.

STATEMENT REGARDING FEDERALLY SPONSORED RESEARCH & DEVELOPMENT

This invention was made with government support under HL134635 awarded by the National Institutes of Health. The government has certain rights in the invention.

FIELD

The present disclosure generally relates to ultrasound imaging. More particularly, this disclosure relates to systems and methods augmented reality integration for ultrasound imaging and ultrasound-guided procedures

BACKGROUND

There are many clinical situations where the benefits of ultrasound imaging are well documented. Ultrasound guidance has been demonstrated to decrease complications and reduce overall costs in procedures such as central venous catheterization, thoracentesis, and paracentesis. Despite these well-documented benefits, there is evidence that ultrasound guidance is underutilized even in clinical situations where its benefits are well documented. For example, an estimated 20-55% of central venous catheter insertions in the internal jugular vein are performed without ultrasound guidance.

Ultrasound utilization depends on many factors including clinical evidence, reimbursement, equipment availability, and provider training. Physician survey studies have found that insufficient training and inability to operate ultrasound systems are frequently cited barriers to its use. As ultrasound use continues its expansion to new groups of providers and clinical uses, the impact of provider training and skill on ultrasound utilization and effectiveness will increase.

Ultrasound-guided procedures such as central venous catheterization (CVC) require a high degree of skill and coordination. The sonographer must mentally create a 3-dimensional representation of anatomy from a series of 2-dimensional images as the probe is rotated, tilted, and translated across the patient's body. As the clinician advances the needle, the probe may be simultaneously tilted or translated to track the needle tip. The clinician's mental representation must account for how motor movement affects the needle relative to the patient's anatomy and relative to the 2D coordinates of the ultrasound images. An additional mental and ergonomic complexity is that the sonographer is required to continuously shift focus between the patient and the ultrasound screen, which may not be optimally positioned due to space constraints.

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

SUMMARY

One aspect of this disclosure is a mixed reality (MR) visualization system including an MR device comprising a holographic display configured to display a holographic image to an operator, a hand-held ultrasound imaging device configured to obtain a real-time ultrasound image of a subject's anatomy, and a computing device communicatively coupled to the MR device and the hand-held ultrasound imaging device. The computing device includes a non-volatile memory and a processor. The computing device is configured to receive the real-time ultrasound image, determine a real-time 3D position and orientation of the hand-held ultrasound imaging device, generate a modified real-time ultrasound image by modifying the real-time ultrasound image to correspond to the real-time 3D position and orientation of the hand-held ultrasound imaging device, and transmit the modified real-time ultrasound image to the MR device for display as the holographic image positioned at a predetermined location relative to the hand-held ultrasound imaging device.

Another aspect of the disclosure is a computer-implemented method of MR visualization of a real-time ultrasound image using a system including a computing device communicatively coupled to a hand-held ultrasound imaging device and a mixed reality (MR) device including a holographic display. The hand-held ultrasound imaging device is configured to obtain the real-time ultrasound image. The method includes receiving, using a computing device, the real-time ultrasound image of a subject's anatomy, determining, using the computing device, the real-time 3D position and orientation of the hand-held ultrasound imaging device, generating, using the computing device, a modified real-time ultrasound image by modifying the real-time ultrasound image to correspond to the real-time 3D position and orientation of the hand-held ultrasound imaging device, and transmitting, using the computing device, the modified real-time ultrasound image to the MR device for display as a holographic image positioned at a predetermined location relative to the hand-held ultrasound imaging device.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

BRIEF DESCRIPTION OF THE DRAWINGS

FIG. 11 is a flow chart illustrating a process of calculating a real-time 3D position and orientation of a hand-held ultrasound imaging device in accordance with one aspect of the disclosure.

The accompanying drawings are included to provide a further understanding of the disclosure and are incorporated in and constitute part of this specification, illustrate several embodiments of the disclosure and together with the description serve to explain the principles of the disclosure.

In the following detailed description of the preferred embodiments, reference is made to the accompanying drawings, which form a part hereof: and within which are shown by way of illustration specific embodiments by which the disclosure may be practiced. It is to be understood that other embodiments may be utilized and structural changes may be made without departing from the scope of the disclosure.

Like reference symbols in the various drawings indicate like elements.

DETAILED DESCRIPTION

Figure 9:
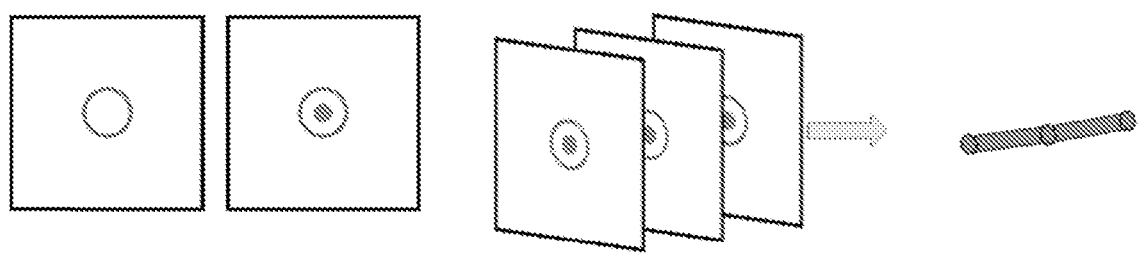
FIG. 9 is a schematic diagram illustrating the process of selecting and combining landmarks in different ultrasound image views to create a virtual image landmark and/or volume for display within the holographic image.

In various aspects, a system for improving the quality, stability, accuracy, and utility of a mixed reality display of spatially tracked clinical tools in a mixed reality (MR) software system is disclosed. The MR system provides a real time 3-dimensional visualization of a 2D ultrasound image plane obtained using a hand-held ultrasound imaging device in the form of a holographic image viewable through a wearable holographic display. In various aspects, the holographic display may further include additional information in the form of menus, data displays, and/or icons indicative of additional information for providing relevant information and/or guidance for the ultrasound imaging and related procedures including, but not limited to, surgical procedures, catheterizations, needle insertions, and any other ultrasound-guided procedure. In other aspects, the MR system may enable the user to define points or regions of interest a first ultrasound image plane that may be combined with points or regions defined in additional ultrasound image planes obtained from different spatial locations. This enables the user to collectively visualize as 3-dimensional lines or volumes within the holographic image that may be used to guide the user in performing ultrasound imaging and related procedures, as illustrated in FIG. 9.

The disclosed MR system provides for the adoption of ultrasound imaging by a broader population of practitioners with varying degrees of experience and training, for example by lowering the skill barrier required for ultrasound-guided procedures device insertion during a central venous catheterization (CVC). To facilitate the integration of the ultrasound images and patient anatomy during an ultrasound-guided procedure, users wear a 3D-MR headset that displays a hologram of the image plane at its true spatial location at the tip of the ultrasound plane. The holographic plane gives users a spatial understanding of the 3D location of the image and the anatomy. This spatial information is particularly valuable for ultrasound-guided procedures such as CVC insertion because it improves the user's understanding of the relationship between the ultrasound image plane, the needle tip, and surrounding anatomy. Although some aspects of this disclosure are described with reference to CVC, the systems and methods of this disclosure may be used for any ultrasound procedure, and particularly for any procedure that uses ultrasound imaging for interventional guidance.

The term "mixed reality", as used herein refers to an augmented reality display method that specifically includes an ability for a user or operator to interact with the computer-generated elements.

"Augmented reality", as used herein, refers to a method of displaying and/or interacting with one or more elements representing computer-generated data. Augmented reality is a blend of virtual reality and real life, wherein a typical augmented reality display includes one or more computer-generated elements displayed to overlay the real-life objects visible by an operator.

"Virtual reality", as used herein, refers to a method of displaying and/or interacting with one or more elements representing computer-generated data. Typically, all elements visible within a field of view of a virtual reality display are computer-generated elements.

When the terms "mixed reality", "virtual reality", and/or "augmented reality" are used herein, it should be understood to encompass all types of modified realities, unless specifically distinguished.

"Holographic display", as used herein, refers to a method of displaying and/or interacting with a virtual 3D object in which the virtual 3D object is dynamically updated to modify an operator's view of the virtual 3D object in response to movements of the operator, or operator requested modifications of the view of the virtual 3D object, such as magnified/reduced, translated/rotated, and/or modified rendering views of the virtual 3D object. Non-limiting examples of virtual 3D objects that may be included in the holographic display of the MR system include ultrasound images, icons indicative of the positions of surgical instruments, control icons, text displays, and any other suitable virtual 3D object without limitation.

Figure 1:
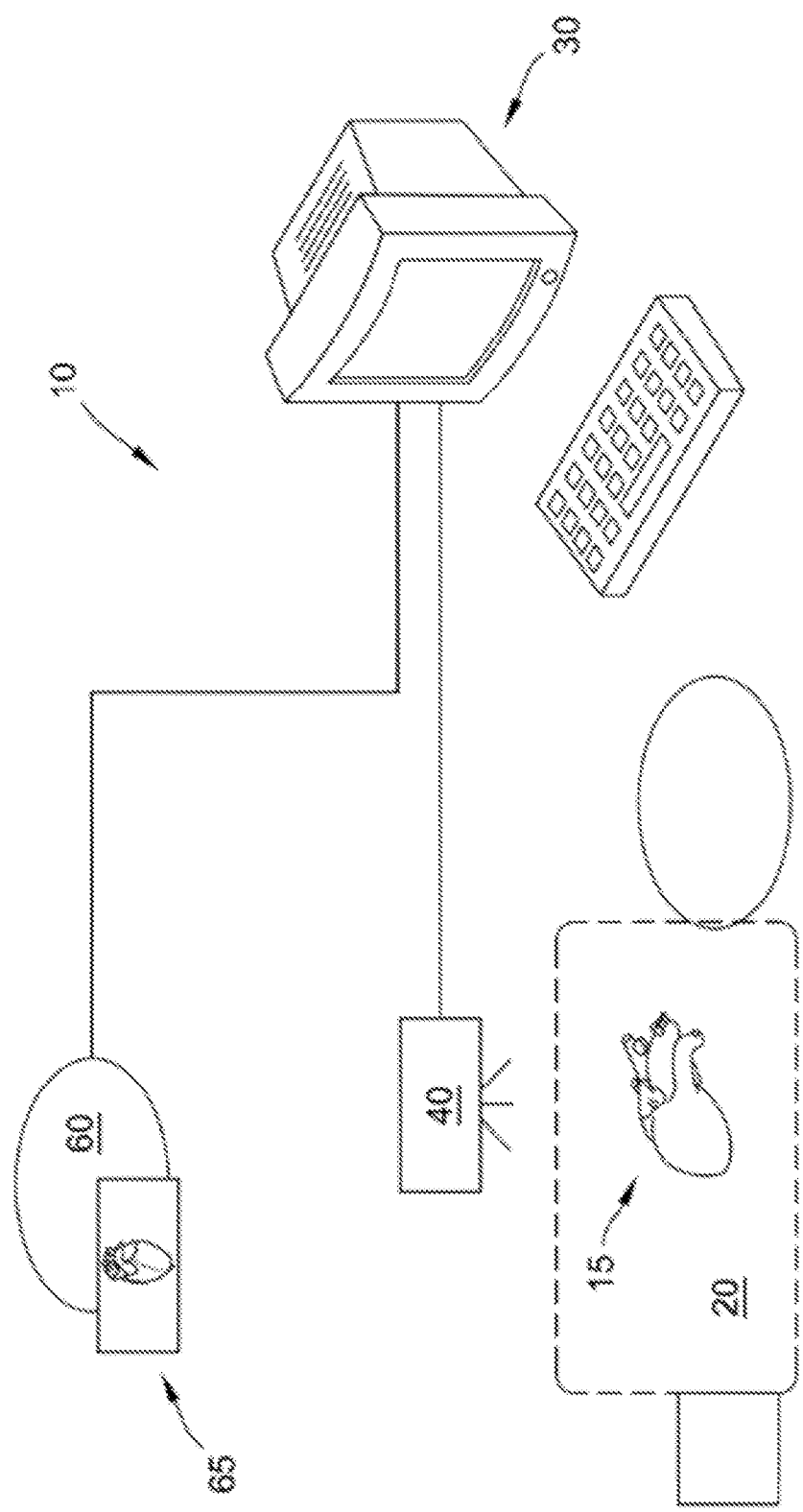
FIG. 1 is a schematic diagram illustrating the elements of an MR system in accordance with one aspect of the disclosure.

FIG. 1 is a schematic diagram of an example MR visualization system 10 (also referred to herein as an MR system 10 or system 10) for visualization and manipulation of ultrasound imaging data as well as additional information including, but not limited to, 2D imaging data, user-identified points or volumes of interest, surgical instrument locations, orientation of the hand-held ultrasound imaging device, vital sign data, and subject demographic data in association with medical diagnostic and treatment procedures that occur within hard to view/access portions of a subject's anatomy. By way of non-limiting example, the MR system 10 can be utilized for procedures within any regions of a patient compatible with ultrasound imaging including, but not limited to, heart, gastrointestinal system, circulatory vessels such as arteries and veins, and other anatomical structures or biological systems. While the embodiments described below are directed to a MR system 10 associated with 3D ultrasound visualization of various procedures, one skilled in the art would recognize that using other 3D localization or pose estimation modalities, including, but not limited to, impedance-based localization, magnetic localization, marker-based localization in combination with the MR system 10 described herein could be readily extended to diagnostic or interventional procedures in other organ systems and/or other anatomical regions.

The MR system 10 includes a hand-held ultrasound imaging device 40 that captures a series of real-time 2D ultrasound images 15 of a patient 20 (e.g. a subject) using any suitable ultrasound imaging techniques. Although a human heart is shown as the ultrasound image 15 in FIG. 1 for illustrative purposes, it should be understood that the ultrasound imaging device 40 may produce ultrasound images 15 of any suitable organ, body part, or portion of the patient 20. For example, during use in CVC, the ultrasound image 15 may be an image of a vein. The MR system further includes a computing device 30 operatively connected to the hand-held ultrasound imaging device 40 and an MR device 60 worn by the system user or operator. The computing device 30 receives the real-time ultrasound images 15 and real-time 3D positions and orientations of the hand-held ultrasound imaging device 40 relative to the MR device 60. The computing device registers the real-time ultrasound images 15 relative to the real-time 3D position and orientation of the hand-held ultrasound imaging device 40 and generates a holographic image 65 for display to the user via the MR device 60. In one aspect, the holographic image 65 includes a hologram of the ultrasound image plane positioned at the tip of the ultrasound probe, so that the spatial location of the displayed ultrasound image corresponds to the true spatial location of the region of the patient imaged using the hand-held ultrasound imaging device 40. In other embodiments, the computing device 30 may be omitted, and the steps described herein as performed by the computing device 30 may be performed by the ultrasound imaging device 40, the MR device 60, or a combination of the two. In still other embodiments, the computing device 30 may be embodied in an ultrasound imaging system that includes the ultrasound imaging device.

In the example embodiment, the MR device 60 is a wearable, MR headset. That the MR device 60 is configured (e.g., sized, shaped, etc.) to be worn on the head of a user similar to a pair of eyeglasses. The MR device 60 includes one or more transparent displays that are positioned in front of the eyes of the user when the user is wearing the MR device 60. The user is able to see through the transparent display(s) and view the real world through the transparent display(s). The MR device 60 displays the holographic image 65 on the transparent display(s) in a location on the display(s) such that splays the holographic image 65 appears to the user to be positioned in the real world at the appropriate real world location. Thus, the mixed reality view seen by the user through the MR device includes a combination of the real world seen through the display(s) and the holographic image 65 displayed on the display(s). In other embodiments, the MR device 60 is not a wearable MR device. For example, in some embodiments, the MR device may include a large transparent display be positioned in front of the user (such as positioned on a table or a support arm) and through which the user may view the real world and on which the holographic image may be displayed.

Figure 2:
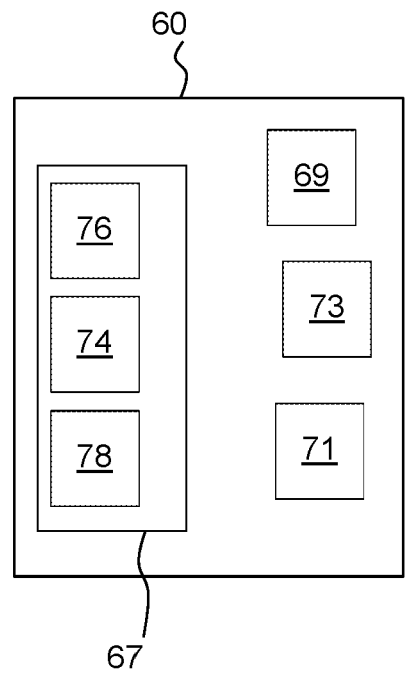
FIG. 2 is a block diagram of an example MR device shown in FIG. 1.

FIG. 2 is a block diagram of an example MR device 60 configured to be worn by a user of the system. The MR device 60 includes an MR controller 67. A first transparent display 69, a second transparent display 71, and a camera 73 are communicatively coupled to the controller 67.

The controller 67 includes a processor 74, a memory 76, and a communication interface 78. The memory 76 stores instructions that program the processor 74 to perform as described herein. That is, the instructions configure the processor 74, and thereby the MR device 60, to perform as described herein. Generally, the instruction cause the processor to determine a view of the user based on images captured by the camera 73, and display the holographic image 65 on the appropriate one or both of the first and second transparent displays 69, 71. In other embodiments, the controller 67 is separate from the wearable MR device 60, but is communicatively coupled to the MR device. The communication interface 78 is a wired or wireless communication interface that allows the controller to communicate with devices remote from the MR device 60, such as the computing device 30, the ultrasound imaging device 40, or any other suitable remote device.

The first transparent display 69 and the second transparent display 71 are positioned in front of the left and right eyes, respectively, of the user when the MR device 60 is worn on the head of the user. In other embodiments, the MR device 60 includes a single transparent display that is positioned in front of both the left and right eyes of the user when the MR device 60 is worn on the head of the user. The first transparent display 69 and the second transparent display 71 are transparent to the user, allowing the user to view the real world through the first transparent display 69 and the second transparent display 71. The controller 67 causes the holographic image 65 to be projected on the first transparent display 69 and the second transparent display 71. In some embodiments, the MR device 60 includes one or more displays, such as liquid crystal displays (LCDs) and a projection system to project the image from the LCDs onto the first transparent display 69 and/or the second transparent display 71. That is, the image to be displayed as the holographic image 65 is displayed on the LCD(s) and the displayed image is projected onto the appropriate location(s) on the first transparent display 69 and/or the second transparent display 71 to appear as the holographic image 65. In some embodiments, the transparency of the first transparent display 69 and the second transparent display 71 is adjustable, so that a user may adjust how much light from the real world is received through the first transparent display 69 and the second transparent display 71.

The camera 73 is a visible light camera positioned on the MR device 60 facing away from the user (when the user is wearing the MR device 60) and is operable to image an outside scene. Therefore, the camera 73 images an outside scene, which is a real scene on the outside in a line of sight direction of the user, and acquires a captured image, which is an image captured by the camera 73, when the user wears MR device 60 on the head. The camera may be any suitable camera, include a CCD camera, a CMOS camera, and the like. In the example embodiment, a single camera 73 is used, and the single camera 73 is positioned to be located in the center of the MR device 60 between the first transparent display 69 and the second transparent display 71 so as to be located approximately between the eyes of the user when the user is wearing the MR device 60. Thus, the image captured by the camera 73 may approximate the view of the real world seen by the user through the first transparent display 69 and the second transparent display 71. In other embodiments, two or more cameras 73 may be included in the MR device 60, and the cameras may be positioned in different locations. Using two or more cameras, may allow for stereo camera vision and may allow for improved detection of spatial relationships (including distance of an object from the user). Further, some embodiments include one or more non-visible light cameras, such as infrared cameras. The infrared camera(s) may replace the visible light camera 73, or may be used in addition to the visible light camera 73

In some embodiments, the MR device 60 includes an inertial measurement unit (IMU), not shown. The IMU is an inertial sensor that detects acceleration. The IMU may detect angular velocity and terrestrial magnetism in addition to the acceleration. Therefore, the IMU may detect acceleration, angular velocity, and terrestrial magnetism of MR device 60, which may be used as part of the detection of the position and movement of the MR device 60 (for example, when the user moves his/her head while wearing the MR device 60).

Figure 3:
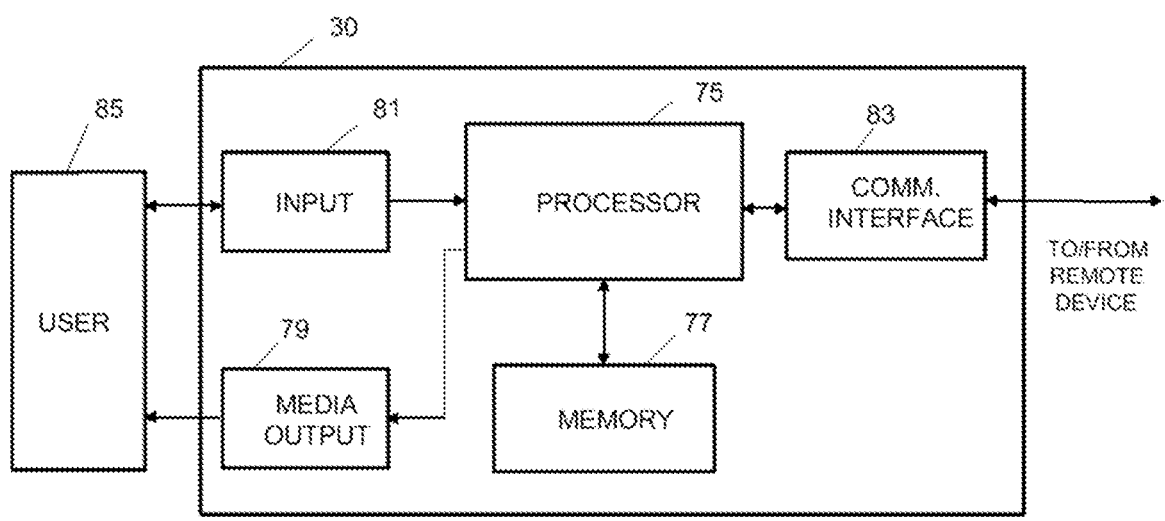
FIG. 3 is a block diagram of the computing device shown in FIG. 1.

FIG. 3 is a block diagram of the computing device 30. The computing device 30 includes a processor 75, a memory 77, a media output component 79, an input device 81, and a communications interface 83. Other embodiments include different components, additional components, and/or do not include all components shown in FIG. 8.

Computing device 30 includes a processor 75 for executing instructions. In some embodiments, executable instructions may be stored in a memory area 77. Processor 75 may include one or more processing units (e.g., in a multi-core configuration). Memory area 77 may be any device allowing information such as executable instructions and/or other data to be stored and retrieved. Memory area 77 may include one or more computer readable media.

In the example embodiment, computing device 30 includes a media output component 79 for presenting information to a user, such as user 85. Media output component 79 may be any component capable of conveying information to user 85. In some embodiments, media output component 79 may include an output adapter such as a video adapter and/or an audio adapter. An output adapter may be operatively coupled to processor 75 and operatively coupled to an output device such as a display device (e.g., a liquid crystal display (LCD), a light emitting diode (LED) display, an organic light emitting diode (OLED) display, a cathode ray tube (CRT) display, an "electronic ink" display, a projected display, etc.) or an audio output device (e.g., a speaker arrangement or headphones). Media output component 79 may be configured to, for example, display a status of the model. In another embodiment, media output component 79 may be configured to, for example, display a result of an image classification process.

Computing device 30 also includes an input device 81 for receiving input from user 85. Input device 81 may include, for example, a keyboard, a pointing device, a mouse, a stylus, a touch sensitive panel (e.g., a touch pad or a touch screen), or an audio input device. A single component, such as a touch screen, may function as both an output device of media output component 79 and an input device of input device 81.

Computing device 30 also includes a communication interface 83, which can be communicatively coupled to a remote device, such as the MR device 60 and/or the ultrasound imaging device 40 of FIG. 1. Communication interface 83 may include, for example, a wired or wireless network adapter or a wireless data transceiver for use with a mobile phone network (e.g., Global System for Mobile communications (GSM), 3G, 4G, or Bluetooth) or other mobile data networks (e.g., Worldwide Interoperability for Microwave Access (WIMAX)). The systems and methods disclosed herein are not limited to any certain type of short-range or long-range networks.

Stored in memory area 77 may be, for example, non-transitory computer readable instructions that cause to processor to perform actions as described herein. That is, the instructions configure the computing device to perform the operations described herein.

Memory area 77 may include, but is not limited to, random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAN). The above memory types are example only, and are thus not limiting as to the types of memory usable for storage of a computer program.

Figure 4:
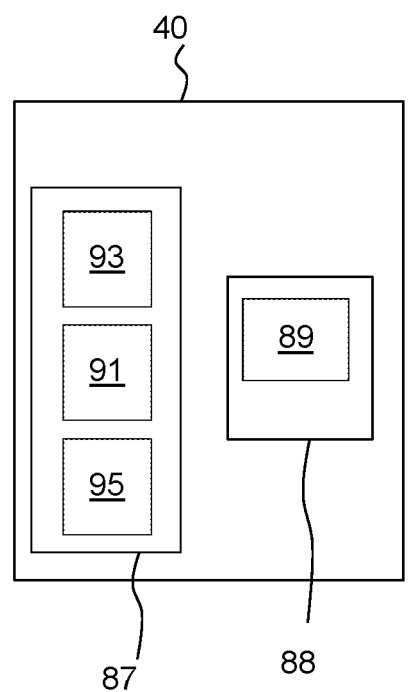
FIG. 4 is a block diagram of the ultrasound imaging device shown in FIG. 1.

FIG. 4 is a block diagram of an example ultrasound imaging device 40. The ultrasound imaging device 40 may be a two dimensional ultrasound imaging device or a three dimensional ultrasound imaging device. The ultrasound imaging device 40 includes an ultrasound controller 87 and a handheld probe 88. The handheld probe 88 includes an IMU 89 communicatively coupled to the ultrasound controller 87. The handheld probe 88 also includes components (not shown) to allow the ultrasound imaging device to capture ultrasound images, such as ultrasound transducer(s) for outputting ultrasound signals and receiving reflected ultrasound signals, an acoustic lens for transmitting ultrasound signals in and out of the ultrasound imaging device, and the like. Some embodiments do not include the IMU 89.

The controller 87 includes a processor 91, a memory 93, and a communication interface 95. The memory 93 stores instructions that program the processor 91 to perform as described herein. That is, the instructions configure the processor 91, and thereby the ultrasound imaging device 40, to perform as described herein. Generally, the instruction cause the processor to control the components of the ultrasound imaging device 40 to generate ultrasound images by outputting ultrasound signals, receive reflected ultrasound signals, generate an image based on the transmitted and received ultrasound signals, and transmit the generated image to the computing device 30. In other embodiments, the ultrasound imaging device 40 does not generate the ultrasound image, but transmits the ultrasound signals to a remote device, such as computing device 30, which generates the ultrasound image based on the ultrasound signals. In some embodiments, the controller 87 is separate from the ultrasound imaging device 40, but is communicatively coupled to the ultrasound imaging device 40. The communication interface 95 is a wired or wireless communication interface that allows the controller 87 to communicate with devices remote from the ultrasound imaging device 40, such as the computing device 30, the MR device 60, or any other suitable remote device. In some embodiments, the controller 87 is included within the handheld probe 88.

In some embodiments, the ultrasound imaging device 40 includes an image registration target (not shown in FIG. 4)

positioned on an outside of the handheld probe 88 to be visible to the user (and thereby to the MR device 60) when the user is using the handheld probe 88. The image registration target may be any suitable marker that is detectable by the MR device, including a one dimensional bar code (e.g., a barcode), a two dimensional bar code (e.g., a QR code), a distinctive image, or the like.

Figure 5:
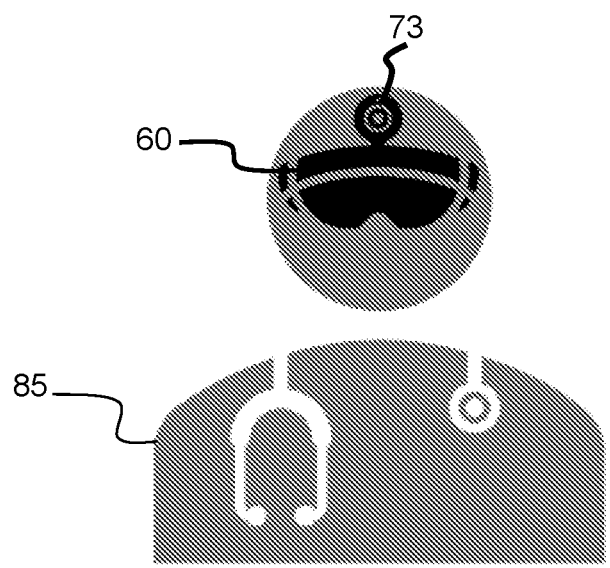
FIG. 5 is a schematic diagram illustrating an MR device with a forward-facing camera in accordance with one aspect of the disclosed MR system.

In various embodiments, the user wears the transparent MR headset 60 (see FIG. 5) and uses a hand-held probe 88 of the ultrasound imaging device 40 (see FIG. 6) to obtain a series of real-time ultrasound images. The ultrasound images are transmitted to the MR device 60, and the MR device adjusts the images for display as a hologram oriented in the ultrasound image plane as viewed by the user/wearer of the MR device 60. The MR device 60 displays the hologram of the ultrasound image plane positioned such that the user sees the ultrasound image in the ultrasound image plane at the tip of the ultrasound probe 88.

Figure 6:
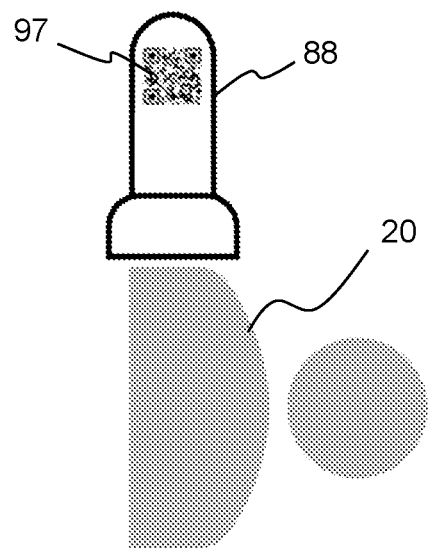
FIG. 6 is a schematic diagram illustrating a hand-held ultrasound imaging device with an attached image registration target and inertial measurement unit (IMU) in accordance with one aspect of the disclosed MR system.
Figure 7:
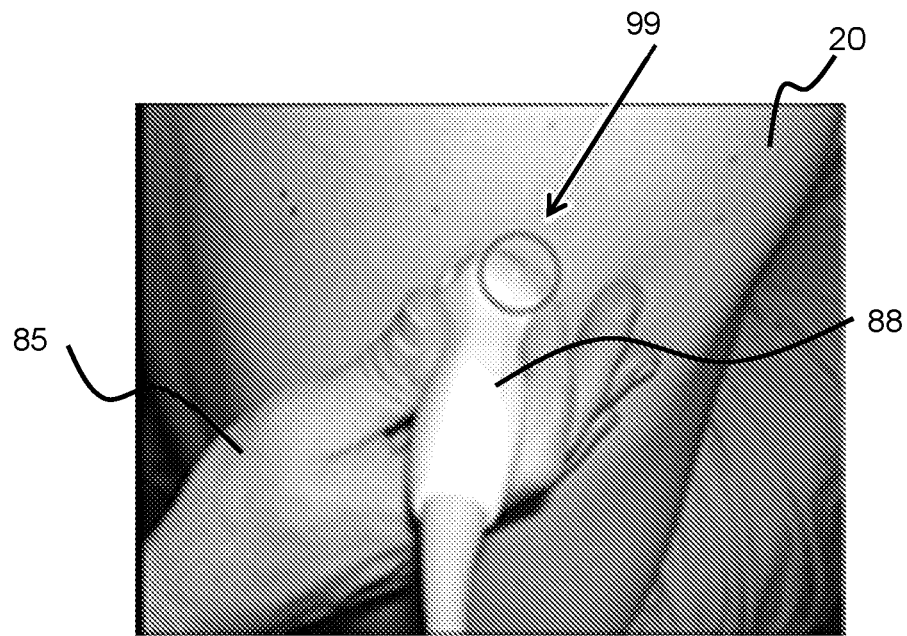
FIG. 7 is an image illustrating the arrangement of the hand-held ultrasound imaging device on a subject during acquisition of a real-time ultrasound image.

As illustrated in FIG. 7, the user operates the handheld ultrasound probe 88 to acquire a series of real-time ultrasound images of the patient 20. The ultrasound image plane is a plane of the handheld ultrasound probe 88 extending out from the tip of the handheld ultrasound probe 88. To ensure proper positioning of the ultrasound image within the holographic display of the MR device 60, the real-time 3D position and orientation of the ultrasound probe 88 relative to the MR headset 60 are tracked. In some embodiments, the position and orientation of the ultrasound probe 88 are tracked by obtaining and analyzing images of an image registration target 97 affixed to the ultrasound probe 88 as illustrated in FIG. 6. The image registration target is viewed by the camera 73 on the MR device 60. By way of non-limiting example, a computer vision algorithm is run on the MR device 60 to compute the position and orientation of the ultrasound probe 88 relative to the MR device 60 based on images of the image registration target 97 obtained by the front-facing camera of the MR device 60. As seen in FIG. 7, the probe 88 includes a notch 99. Ultrasound images frequently include a marker indicating the position of the notch 99 relative to the ultrasound image to aid the operator in mentally orienting the 2D ultrasound image to the real world location of the probe 88.

In various embodiments, a custom image filter that runs on the computing device 30 streams the ultrasound image data acquired by the ultrasound imaging device 40 to the MR device 60 in real-time. Software that runs on the computing device 30 and/or MR device 60 registers the real-time ultrasound image data to correspond to the 3D position and orientation data of the ultrasound probe 88 to display a hologram of the ultrasound image plane at the tip of the probe 88, a position indicative of the physical location of the ultrasound data within the subject. In various embodiments, the position of the hologram updates in real-time as the user moves the ultrasound probe 88, as the MR device 60 moves (e.g. as the user moves) and the image updates in real-time as image data is acquired.

The MR system 10 may include multiple MR devices 60. By way of non-limiting example, a first operator operating the hand-held ultrasound imaging device 40 may wear a first MR device 60 including, but not limited to, a first head-mounted display, and a second operator may wear a second MR device 60 including, but not limited to, a second head-mounted display. In this non-limiting example, the first and second operators may perform a surgical procedure together on a patient. The first and second MR devices 60 may display different views of the same holographic image 65 of the patient 20. For instance, displayed views of the holographic image 65 may positioned at different angles based on the location of each corresponding MR device 60 relative to the patient 20.

In some embodiments, the holographic image 65 may consist solely of the real-time ultrasound image 15. In other embodiments, the computing device 30 of the MR system 10 may receive additional data that may be incorporated into the holographic image for display to the operator on the holographic display of the MR device 60 as described below.

The additional data received by the computing device 30 of the MR system 10 and incorporated into the holographic image may include: real-time 3D data defining positions and/or measured values within the coordinate system defining the holographic display; real-time numerical measurements such as one or more vital signs; pre-determined data such as patient demographic data, and any combination thereof. In these various other aspects, the additional data may be incorporated and/or overlaid on the ultrasound image within the holographic display, or the additional data may be displayed as one or more separate element within the holographic image as described in additional detail below.

In some embodiments, the MR system 10 may further include an instrument position sensor configured to obtain at least one real-time 3D position of at least one surgical instrument, including, but not limited to, a central venous catheter. In this aspect, computing device 30 may receive the real-time 3D position of the surgical instrument and generate the holographic image that includes an icon indicative of the real-time position of the at least one surgical instrument overlaid on the ultrasound image within the holographic display (i.e., on MR device 60). In another aspect, the real-time 3D position of the surgical instrument may be obtained using a separate device including, but not limited to a separate instrument position sensor of a surgical instrument system. Non-limiting examples of suitable instrument position sensors include an electroanatomic mapping devices as well as position sensing devices that make use of ultrasound, magnetic fields, electrical fields, and/or any other existing suitable position sensing method.

In some embodiments, the MR system 10 is configured to receive cues (e.g., signals, gestures, indications, inputs, vocal comments, etc.) from an operator of the MR system 10. In response to one or more cues from the operator, the computing device 30 or the MR device 60 may modify the holographic image 65 as displayed on the MR device 60 according to the preferences of the operator. By way of non-limiting example, the operator may enlarge, reduce, rotate, or move the holographic image as displayed on the holographic display to facilitate the accomplishment of a diagnostic and/or surgical procedure. The cues may be provided using an input device, such as a keyboard, mouse, joystick, or the like, or by performing gestures that may be captured by the camera 73. However input, the MR device 60 (or the computing device 30), interprets the gesture and appropriately modifies the holographic image. For example, the operator may make a pinching gesture with the operator's fingers in front of the MR device 60 so that the operator appears to be pinching the holographic image 65. In response, the MR system 10 may reduce the size of the holographic image. In some embodiments in which the MR system 10 includes multiple MR devices 60, a first MR device 60 worn by a first operator may be operatively coupled to the computing device 30 such that only the first operator may modify the holographic image as displayed on all holographic displays of all MR devices 60 of the MR system 10. In these various other aspects, the computing device 30 may receive the relative positions and orientations of each of the multiple MR devices 60 and generate a holographic image for each MR device 60 corresponding to each position and each orientation of each MR device 60 relative to the first MR device 60 worn by the first operator, who also controls modifications of the holographic image.

Figure 8:
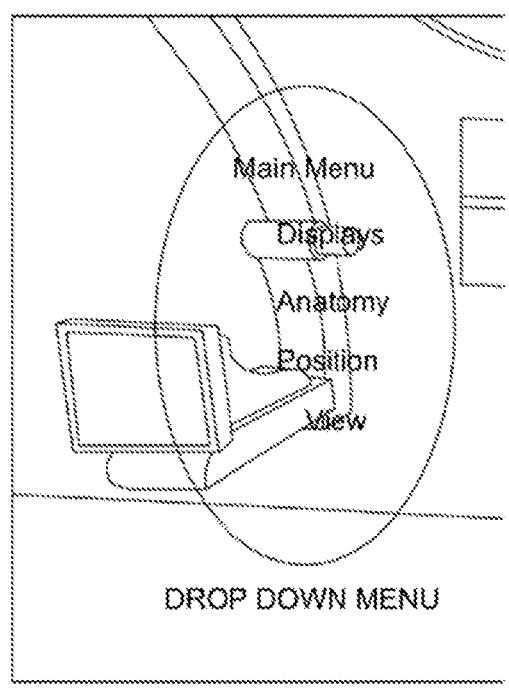
FIG. 8 is an image of a view provided to the operator of the MR system that includes a drop-down menu in accordance with one aspect of the disclosure.

In some embodiments, the computing device 30 may generate a menu or other image element that includes user-selectable elements displayed in the form of a non-transparent or transparent row or column of alphanumeric strings, symbols, and/or icons. In these additional aspects, the user-selectable elements provide a means of selecting one or more instructions to be executed by one or more processors of the computing device 30 to enable the operation of the MR system 10. By way of non-limiting example, the computing device 30 may generate a transparent menu within the holographic image as illustrated in FIG. 8.

By selecting one or more of the interactive menu elements within the holographic image, the operator of the MR device 60 can also view and interact with the holographic display 65 and additional information without having to break sterility or communicate with anyone present during a diagnostic or surgical procedure. As disclosed herein, the MR device 60 can present and remove the information as needed in a true mixed reality environment depending on the needs of the operator of the MR system 10. In one aspect, an arrangement of elements within the holographic image may be saved by the computing device 30 and retrieved by the MR system 10 for subsequent use by the same operator as a preferred arrangement of elements.

In some embodiments, the computing device 30 may receive an indication of a user input (i.e. a cue) from the MR device 60 or a separate input device (e.g., a camera or motion sensor) to select two or more ultrasound images obtained using the hand-held ultrasound imaging device for simultaneous display within the holographic display. By way of non-limiting example, the two or more ultrasound images may be displayed simultaneously to guide a user through a planned needle trajectory.

In some embodiments, the computing device 30 may receive an indication of a user input (i.e. a cue) from the MR device 60 or a separate input device (e.g., a camera, motion sensor, mouse, keyboard, joystick, etc.) to position virtual markers on one or more ultrasound images within the holographic display, as illustrated in FIG. 9. Based on the user input, the computing device 30 may determine a metric or icon for display on the holographic display along with the ultrasound image. By way of non-limiting example, the virtual markers may be virtual calipers configured to measure a dimension of an anatomical structure within the ultrasound image of the holographic display (e.g. a metric). By way of another non-limiting example, the computing device may allow users to select points or regions from multiple ultrasound images acquired at different locations and may transform the user-selected points or regions into 3-dimensional lines or volumes that are subsequently displayed within the holographic display of the MR device to demarcate important anatomic structures or planned needle trajectories, as illustrated in FIG. 9.

In various embodiments, the computing device 30 may update the holographic image over time to account for changes due to one or more time-varying factors including, but not limited to: section or deselection of a user-selectable menu element by the operator, receipt of updated real-time data such as updated vital signs data, an additional ablation event, a change in other datasets, such as the real-time dataset associated with the fluoroscope imaging. The computing device 30 may update the holographic image to include a representation of a portion of an instrument positioned relative to a patient's organ, e.g., a position of a catheter tip relative to the patient's heart. The computing device 30 may update the holographic image based on sensor data from the instrument indicative of detected motion of the instrument.

In other embodiments, the computing device 30 may receive one or more additional alphanumeric datasets including, but not limited to, a patient demographic dataset and/or real-time measurements of vital signs of the subject obtained from existing vital sign measurement devices. In this other aspect, the one or more additional alphanumeric datasets may be incorporated into the holographic image in the form of a transparent alphanumeric element overlaid within the holographic image.

In additional embodiments, the computing device 30 may receive one or more additional datasets defining at least one additional 2D image obtained from at least one additional medical imaging device. In one aspect, the at least one additional 2D image may include a 2D representation of a 3D real-time image including, but not limited to, a real-time fluoroscope image. In various aspects, the at least one additional 2D image may be incorporated into the holographic image in the form of a 2D visual element overlaid or displayed separately from the 3D model 65. Non-limiting suitable 2D visual elements incorporated into the holographic image include a virtual 2D monitor, an inset image, and any other known representation of a 2D visual element in a 3D holographic image. By way of non-limiting example, an additional dataset defining a real-time fluoroscopic image may be incorporated into the holographic image in the form of an inset image.

Figure 10:
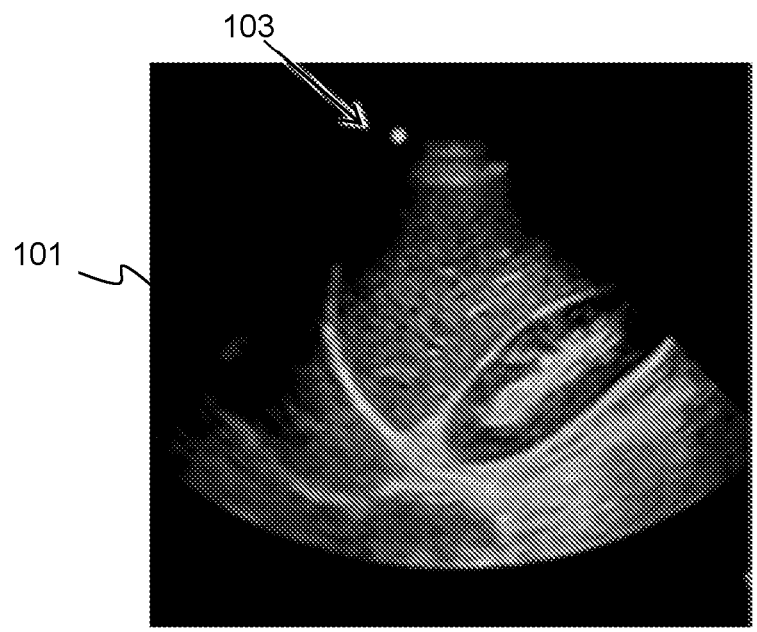
FIG. 10 is an image showing a holographic image that includes a screen marker indicative of a 3D orientation of a hand-held ultrasound imaging device superimposed on a real-time ultrasound image.

In some embodiments, the holographic display may further include an icon indicative of the orientation of the ultrasound probe 88 relative to the user. Ultrasound probes typically have a physical "notch" on one side, as illustrated by notch 99 in FIG. 7. Images displayed on the ultrasound screen typically have a dot displayed on one side (typically the left side). FIG. 10 is an example 2D ultrasound image 101. The dot 103 indicates that side of the image corresponds to the side of the probe 88 with the notch. Because ultrasound probes may be covered with sterile covers during procedures, it can be difficult for the operator to locate the notch. The disclosed MR system 10 may display a holographic notch on the image plane hologram, so the user can quickly see which side of the image plane corresponds to the conventional view.

In various aspects, the MR system may include additional elements and devices to enhance the accuracy and resolution of the real-time 3D position and orientation data for the hand-held ultrasound probe 88. Non-limiting examples of suitable additional elements and devices include the IMU 89 (FIG. 4), an external tracking system, and any other suitable means of obtaining position and orientation data. In some aspects, spatial position and orientation accuracy of hand-held objects may be improved through incorporating the IMU 89 and/or an external tracking system that is registered to the coordinate system of the MR device 60 using a registration image and automated registration procedure. In various aspects, the additional information obtained by the additional devices may be incorporated either periodically or continuously by the MR device 60 to correct or prevent errors due to drift in the spatial tracking. FIG. 11 is a flow chart illustrating a method of combining 3D position and orientation measurements from various devices in one aspect.

Because computer vision is computationally demanding and MR headsets are typically low-powered devices, there can be some lag in displaying the correct probe 88 position and orientation. Additionally, the image target may be partially blocked by the user's hands or other objects during a procedure. In some aspects, the ultrasound probe 88 tracking may be enhanced by incorporating data from the IMU 89. The IMU may be affixed to the ultrasound probe 88 or incorporated within the ultrasound probe 88. The IMU sensor data may be merged with the computer vision algorithm to improve the position and orientation tracking accuracy and decrease tracking latency. In various aspects, the IMU senses forces, angular rate, and orientation of the ultrasound transducer probe. Signals from an IMU may be computationally merged with conventional tracking to improve and stabilize tracking, including situations where line-of-sight to tracking markers or image is temporarily lost. In one aspect, the signals may be combined using Kalman filter or other algorithms.

In various other embodiments, an external tracking system may be incorporated to enhance tracking of the position and orientation of the ultrasound imaging probe. Non-limiting examples of suitable external tracking systems include IR camera arrays, depth cameras, electromagnetic tracking arrays, and any other suitable external tracking system. In some aspects, the external tracking system may make use of the image registration target 97 (see FIG. 6). In other embodiments, the external tracking system may make use of additional attached hardware including, but not limited to, IR markers or using a digitizing probe 88 that can be used to record the coordinates of image features such as corners. In one aspect, the signals from the external tracking system may be combined with the signals based on computer vision analysis of the image registration target and/or signals from the IMU using a Kalman filter or other algorithms.

In still other embodiments, the MR device 60 includes an object detection and pose estimation (ODPE) algorithm that is trained to detect the probe 88 in images captured by the camera 73 and estimate the pose of the probe 88 relative to the MR device 60. For example, the MR device 60 may establish sparse point correspondences between features on a 3D model of the probe 88 and features in the image and solve the perspective-n-point (PnP) problem based on the established correspondences. These correspondences may be established by detecting stable keypoints and matching them using distinctive appearance-based descriptors, such as ORB descriptors. Other embodiments may use any suitable ODPE algorithm for detecting the probe 88 and estimating its pose.

In some aspects, any of the tracking devices and methods described above may be expanded to track a needle or other surgical instrument of known geometry in addition to the ultrasound probe. When performing ultrasound-guided procedures such as biopsies or catheterizations it is difficult to track the needle tip relative to the ultrasound image plane. Tracking the positions of the ultrasound probe 88 and surgical instrument simultaneously allows visualization of the ultrasound imaging plane and the needle even after it has pierced the skin to help the operator implement a surgical procedure.

The disclosed MR system can be used for many ultrasound-guided clinical interventions. In one aspect, the MR system may be used to facilitate vascular access. During these procedures, the ultrasound operator guides a needle into a blood vessel. Use of ultrasound guidance for vascular access improves safety and decreases costs associated with complications. By displaying ultrasound images at the probe tip location, users will have a better spatial understanding of patient anatomy and the location of the ultrasound image plane relative to the probe tip. This will make procedures faster, more intuitive, and safer.

In various embodiments, the MR device 60 can include a true virtual reality (VR) device (i.e., a device that fully immerses the operator in the created environment) or an augment reality (AR) device (i.e., operator can have images or models displayed virtually in the virtual space, but is still able to see and interact with the true environment). Along those lines, the MR device 60 can be a wearable device, including, but not limited to, the Microsoft HOLOLENS™ (i.e. an AR device) and OCULUS RIFT™ (i.e. VR device). The MR device 60 may include sensors such as motion sensors (e.g., accelerometers, gyroscopes, or inertial measurement units), audio sensors, eye and gaze tracking sensors, and/or an electronic display, among other components. In another aspect, the MR device 60 can provide a projected holographic display that includes the 3D model 65. The MR device 60 may be communicatively coupled to the HMD via a wireless exchange protocol, or via a wired connection. In at least some aspects, use of an AR device may be advantageous since it allows the operator to see the patient and interact with the patient in real time while simultaneously viewing and interacting with the 3D model 65 and deriving the benefits of it, making for a safer patient experience.

In such embodiments, the real-time ultrasound image within the holographic image 65 may be rendered as obtuse or semi-transparent depending on the location of the ultrasound imaging probe 88 and/or other surgical instruments, or fully transparent to enable an unimpeded view of the ultrasound imaging probe 88 and/or other surgical instruments. In a transparency view, the operator may change the transparency of various elements of the holographic display using operator-enabled cues received by at least one sensor of the MR device 60, allowing for readily apparent visualization during a diagnostic and/or surgical procedure. In addition, the MR device 60 can also allow the operator to manipulate the position, orientation, and size of the ultrasound image. In addition, the operator can switch between views, as well as data display, without the use of hands so the operator can maintain sterility throughout the entirety of the procedure.

By way of non-limiting example, the MR system 10 may use head and/or eye tracking technology to receive input commands (e.g., user input/cues) from the operator without requiring the operator to physically touch an input device (e.g., MR device 60) using the operator's hands. In some embodiments, the input device is physically connected to the MR device 60. In other embodiments, the input device is separate from the MR device 60 and communicatively coupled to the computing device 30. For example, the input device is a Microsoft KINECT™. The input device may include imaging sensors (e.g., cameras), illumination sources for the imaging sensors, motion sensors, depth sensors, among other components. Based on sensor data, the input device can capture hand gestures and perform posture detection of an operator. In one aspect, the operator-enabled inputs may be derived from modifications of existing operator-enabled inputs provided with the MR device 60.

In addition, a planned mapping in preparation for a procedure may be produced using the ultrasound images in combination with the MR device 60 as described above and illustrated in FIG. 9. In another aspect, virtual calipers (e.g., a ruler) can be displayed by the MR device 60 to allow the operator, in the virtual environment, to make real time, accurate measurements.

The MR system 10 is configured to display virtual, patient-specific ultrasound images in front of interventional physicians (e.g., operators/users) during diagnostic and/or surgical procedures. By using ultrasound images to reveal real-time anatomical structures, improvements in physician training, patient outcomes, and clinician collaboration will occur. Further, the MR system 10 may also reduce the medical and economic burden for a patient who would otherwise undergo multiple procedures that result from poor visualization of their anatomy.

Figure 12:
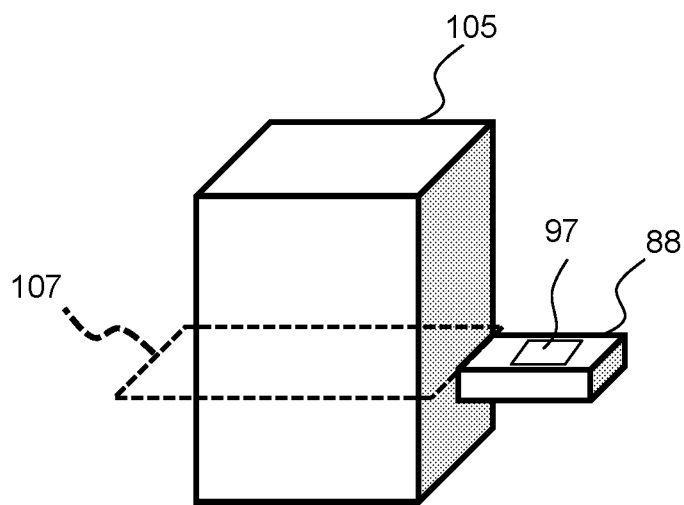
FIG. 12 is a simplified diagram of the ultrasound probe being used to image an object.

FIG. 12 is a simplified diagram of the ultrasound probe 88 being used to image an object 105, and shows the image plane 107 of the ultrasound image that will be produced by the ultrasound imaging device 40. The MR device 60 will modify the generated ultrasound image (e.g., the image 101 in FIG. 10) to be oriented and skewed to appear to the user to lie in the image plane 107 when projected as holographic image 65 on the MR device 60.

Figure 13:
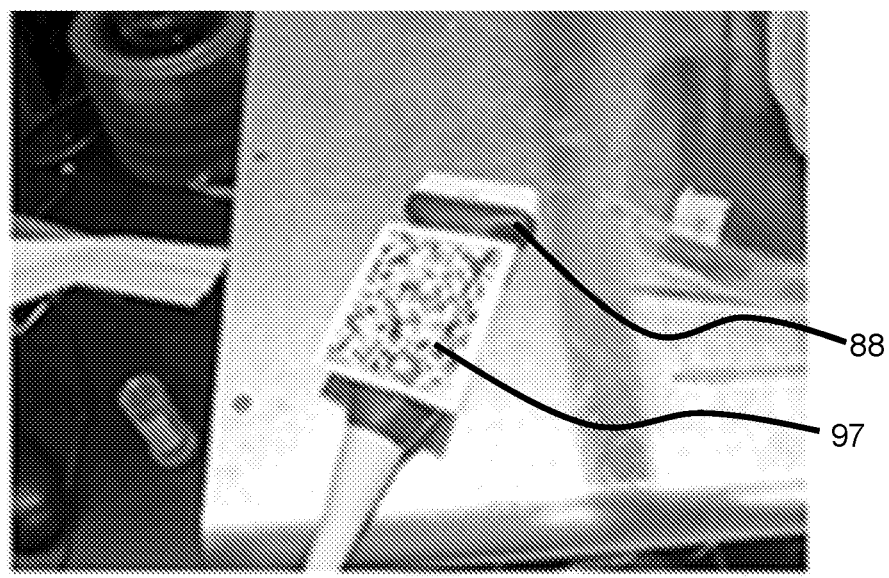
FIG. 13 is an image showing an image registration target attached to the hand-held ultrasound imaging device in accordance with one aspect of the disclosure.
Figure 14:
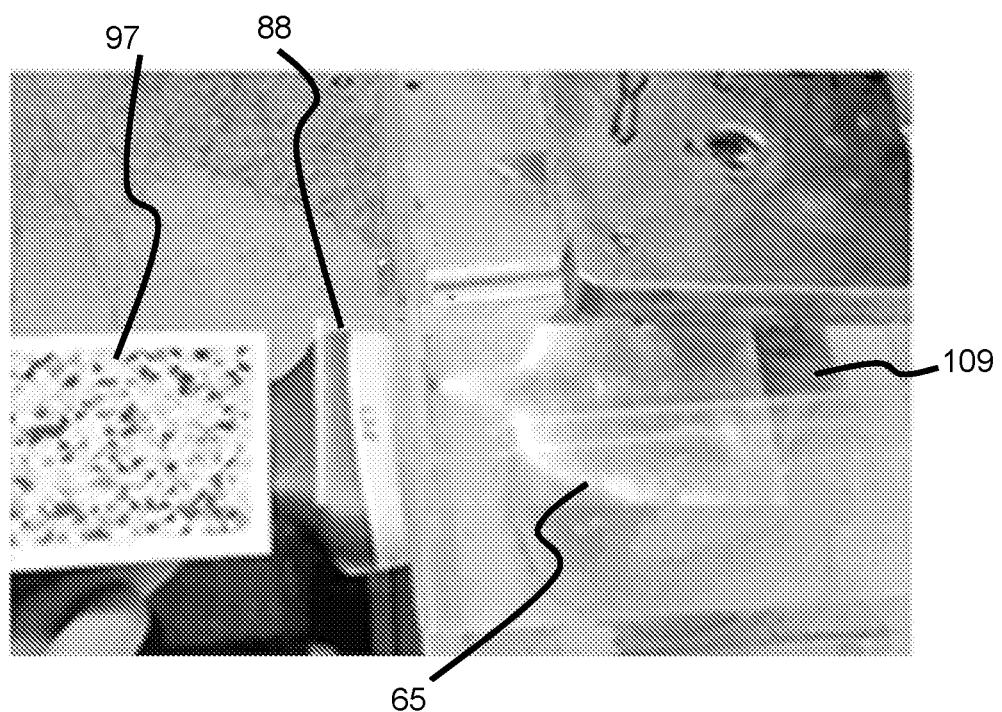
FIG. 14 is an image showing a holographic image, image registration target, and hand-held ultrasound imaging device as viewed through an MR display of the MR system of FIG. 1 in accordance with one aspect of the disclosure.

FIG. 13 is a photograph of an example ultrasound probe 88 including an example image registration target 97 attached thereto. FIG. 14 is a photograph of the view of a user through the MR device 60, showing the example ultrasound probe 88 from FIG. 13 being used to image an object 109. The holographic image 65 is displayed within the image plane of the ultrasound probe 88.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, measurements, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples. As various changes could be made in the above constructions and methods without departing from the scope of the disclosure, it is intended that all matter contained in the above description and shown in the accompanying drawing(s) shall be interpreted as illustrative and not in a limiting sense.

What is claimed is:

1. A mixed reality (MR) visualization system, comprising:
   an MR device comprising a holographic display configured to display a holographic image to an operator;
   a hand-held ultrasound imaging device configured to obtain a real-time ultrasound image of a subject's anatomy; and
   a computing device communicatively coupled to the MR device and the hand-held ultrasound imaging device, the computing device comprising a non-volatile memory and a processor, wherein the computing device is configured to:
receive the real-time ultrasound image;
determine a real-time 3D position and orientation of the hand-held ultrasound imaging device;
generate a modified real-time ultrasound image by modifying the real-time ultrasound image to correspond to the real-time 3D position and orientation of the hand-held ultrasound imaging device; and
transmit the modified real-time ultrasound image to the MR device for display as the holographic image positioned at a predetermined location relative to the hand-held ultrasound imaging device.

2. The system of claim 1, wherein:
the ultrasound imaging device comprises a tracking device for tracking the real-time 3D position and orientation of the hand-held ultrasound imaging device; and
the computing device is configured to determine real-time 3D position and orientation of the hand-held ultrasound imaging device based at least in part on the tracking device.

3. The system of claim 2, wherein:
the tracking device comprises an image registration target attached to the hand-held ultrasound imaging device;
the MR device further comprises a front-facing camera configured to obtain a real-time image of the image registration target; and
the computing device is further configured to determine the real-time 3D position and orientation of the hand-held ultrasound imaging device based at least in part on the real-time image of the image registration target.

4. The system of claim 2, wherein the tracking device includes an inertial measurement unit (IMU) configured to track the real-time 3D position and orientation of the hand-held ultrasound imaging device, and the computing device is further configured to determine the real-time 3D position and orientation of the hand-held ultrasound imaging device based at least in part on the real-time 3D position and orientation of the hand-held ultrasound imaging device tracked by the IMU.

5. The system of claim 1, further comprising an external tracking system configured to track the real-time 3D position and orientation of the hand-held ultrasound imaging device, the external tracking system selected from the group consisting of an IR camera array, a depth camera, an electromagnetic tracking array, and any combination thereof, wherein the hand-held ultrasound imaging device further comprises at least one marker affixed to the hand-held ultrasound imaging device, the at least one marker detectable by the external tracking system, and the computing device is configured to determine real-time 3D position and orientation of the hand-held ultrasound imaging device based at least in part on the real-time 3D position and orientation of the hand-held ultrasound imaging device detected by the external tracking system.

6. The system of claim 5, wherein the tracking device comprises one or both of an image registration target and an inertial measurement unit, and the computing device is configured to calculate a composite real-time 3D position and orientation of the hand-held ultrasound imaging device using a Kalman filter to combine at least two of:
the real-time 3D position and orientation of the hand-held ultrasound imaging device based on a real-time image of the image registration target captured by a camera of the MR device;
the real-time 3D position and orientation of the hand-held ultrasound imaging device tracked by the IMU; and
the real-time 3D position and orientation of the hand-held ultrasound imaging device tracked by the external tracking system.

7. The system of claim 1, wherein the computing device is further configured to:
receive a real-time 3D position of a surgical instrument;
register the real-time 3D position of the surgical instrument relative to the real-time ultrasound image device; and
generate the modified real-time ultrasound image by further modifying the real-time ultrasound image to include an icon superimposed on the real-time ultrasound image, the icon indicative of the real-time 3D position of the surgical instrument.

8. The system of claim 7, wherein the real-time 3D position of the surgical instrument is received from an instrument position sensor of a surgical instrument system operatively coupled to the computing device.

9. The system of claim 1, wherein the MR device is further configured to detect a cue produced by an operator.

10. The system of claim 9, wherein the cue is selected from one or more of a gesture, an eye movement, a voice comment, a facial expression, and a head movement.

11. The system of claim 9, wherein the computing device is further configured to modify the holographic image in response to the cue produced by the operator, the modification comprising at least one of a zoom, a rotation, a translation, a generation of a cross section, and a change of rendering of the real-time ultrasound image.

12. The system of claim 9, wherein the computing device is further configured to modify the holographic image in response to the cue produced by the operator, the modification comprising at least one of:
simultaneously displaying two or more user-selected ultrasound images using the holographic display;
creating at least one icon indicative of a user-selected position or area on at least one real-time ultrasound image for display on the holographic display; and
combining each of the at least one icons to produce a line or volume for display on the holographic display.

13. A computer-implemented method of MR visualization of a real-time ultrasound image using a system including a computing device communicatively coupled to a hand-held ultrasound imaging device and a mixed reality (MR) device including a holographic display, the hand-held ultrasound imaging device configured to obtain the real-time ultrasound image, the method comprising:
receiving, using a computing device, the real-time ultrasound image of a subject's anatomy;
determining, using the computing device, the real-time 3D position and orientation of the hand-held ultrasound imaging device;
generating, using the computing device, a modified real-time ultrasound image by modifying the real-time ultrasound image to correspond to the real-time 3D position and orientation of the hand-held ultrasound imaging device; and
transmitting, using the computing device, the modified real-time ultrasound image to the MR device for display as a holographic image positioned at a predetermined location relative to the hand-held ultrasound imaging device.

14. The method of claim 13, wherein:
the ultrasound imaging device comprises a tracking device for tracking the real-time 3D position and orientation of the hand-held ultrasound imaging device; and
determining the real-time 3D position and orientation of the hand-held ultrasound imaging device comprises determining the real-time 3D position and orientation of the hand-held ultrasound imaging device based at least in part on the tracking device.

15. The method of claim 14, wherein:
the tracking device comprises an image registration target attached to the hand-held ultrasound imaging device, the MR device further comprises a front-facing camera configured to obtain a real-time image of the image registration target; and
determining the real-time 3D position and orientation of the hand-held ultrasound imaging device comprises determining the real-time 3D position and orientation of the hand-held ultrasound imaging device based at least in part on the real-time image of the image registration target.

16. The method of claim 14, wherein:
the tracking device includes an inertial measurement unit (IMU) configured to track the real-time 3D position and orientation of the hand-held ultrasound imaging device; and
determining the real-time 3D position and orientation of the hand-held ultrasound imaging device comprises determining the real-time 3D position and orientation of the hand-held ultrasound imaging device based at least in part on the real-time 3D position and orientation of the hand-held ultrasound imaging device tracked by the IMU.

17. The method of claim 13, wherein:
the system further comprises an external tracking system configured to track the real-time 3D position and orientation of the hand-held ultrasound imaging device, the external tracking system selected from the group consisting of an IR camera array, a depth camera, an electromagnetic tracking array, and any combination thereof, wherein the hand-held ultrasound imaging device further comprises at least one marker affixed to the hand-held ultrasound imaging device, the at least one marker detectable by the external tracking system; and
determining the real-time 3D position and orientation of the hand-held ultrasound imaging device comprises determining the real-time 3D position and orientation of the hand-held ultrasound imaging device based at least in part on the real-time 3D position and orientation of the hand-held ultrasound imaging device detected by the external tracking system.

18. The method of claim 17, wherein the tracking device comprises one or both of an image registration target and an inertial measurement unit, and determining the real-time 3D position and orientation of the hand-held ultrasound imaging device comprises determining the real-time 3D position and orientation of the hand-held ultrasound imaging device by determining a composite real-time 3D position and orientation of the hand-held ultrasound imaging device using a Kalman filter to combine at least two of:
the real-time 3D position and orientation of the hand-held ultrasound imaging device based on a real-time image of the image registration target captured by a camera of the MR device;
the real-time 3D position and orientation of the hand-held ultrasound imaging device tracked by the IMU; and
the real-time 3D position and orientation of the hand-held ultrasound imaging device tracked by the external tracking system.

19. The method of claim 13, further comprising:
receiving, using the computing device, a real-time 3D position of a surgical instrument;
registering, using the computing device, the real-time 3D position of the surgical instrument relative to the real-time ultrasound image device; and
generating, using the computing device, the modified real-time ultrasound image by further modifying the real-time ultrasound image to include an icon superimposed on the real-time ultrasound image, the icon indicative of the real-time 3D position of the surgical instrument.

20. The method of claim 19, wherein receiving the real-time 3D position of a surgical instrument comprises receiving the real-time 3D position of the surgical instrument from an instrument position sensor of a surgical instrument system operatively coupled to the computing device.

21. The method of claim 13, further comprising receiving, using the computing device, a cue produced by an operator and detected by the MR device.

22. The method of claim 21, wherein receiving the cue comprises receiving a cue selected from one or more of a gesture, an eye movement, a voice comment, a facial expression, and a head movement.

23. The method of claim 21, further comprising modifying, using the computing device, the holographic image in response to the cue produced by the operator, the modification comprising at least one of a zoom, a rotation, a translation, a generation of a cross section, and a change of rendering of the real-time ultrasound image.

24. The method of claim 21, further comprising modifying, using the computing device, the holographic image in response to the cue produced by the operator, the modification comprising at least one of:
simultaneously displaying two or more user-selected ultrasound images using the holographic display;
creating at least one icon indicative of a user-selected position or area on at least one real-time ultrasound image for display on the holographic display; and
combining each of the at least one icons to produce a line or volume for display on the holographic display.

* * * * *